United States Patent
Gunzert et al.

(10) Patent No.: US 7,761,243 B2
(45) Date of Patent: Jul. 20, 2010

(54) MEASURING DEVICE FOR PROCESS ENGINEERING AND OPERATING METHOD FOR A MEASURING DEVICE

(75) Inventors: Michael Gunzert, Talheim (DE); Martin Gehrke, Weinstadt (DE)

(73) Assignee: Endress + Hauser Conducta GmbH + Co. KG, Gerlingen (DE)

(*) Notice: Subject to any disclaimer, the term of this patent is extended or adjusted under 35 U.S.C. 154(b) by 53 days.

(21) Appl. No.: 10/510,072

(22) PCT Filed: Apr. 11, 2003

(86) PCT No.: PCT/EP03/03761

§ 371 (c)(1), (2), (4) Date: Jun. 9, 2005

(87) PCT Pub. No.: WO03/087963

PCT Pub. Date: Oct. 23, 2003

(65) Prior Publication Data
US 2005/0216230 A1    Sep. 29, 2005

(30) Foreign Application Priority Data
Apr. 13, 2002    (DE) .................................. 102 16 332

(51) Int. Cl.
*G01N 31/00* (2006.01)
(52) U.S. Cl. ......................................................... 702/30
(58) Field of Classification Search ................... 702/30
See application file for complete search history.

(56) References Cited

U.S. PATENT DOCUMENTS

| | | | |
|---|---|---|---|
| 4,113,381 A * | 9/1978 | Epstein | 356/5.12 |
| 4,176,403 A | 11/1979 | Suzuki et al. | |
| 4,275,455 A | 6/1981 | Bartlett | |
| 4,864,845 A * | 9/1989 | Chandler et al. | 73/38 |
| 4,937,777 A | 6/1990 | Flood et al. | |
| 5,099,449 A | 3/1992 | Dombrosky et al. | |
| 5,402,685 A * | 4/1995 | Brobeil | 73/861.12 |
| 5,444,644 A | 8/1995 | Divjak | |
| 6,285,964 B1 * | 9/2001 | Babel et al. | 702/121 |
| 6,574,515 B1 | 6/2003 | Kirkpatrick | |
| 6,839,636 B1 * | 1/2005 | Sunshine et al. | 702/22 |
| 2001/0043882 A1 * | 11/2001 | Berger et al. | 422/67 |
| 2003/0186461 A1 * | 10/2003 | Boehr et al. | 436/181 |

FOREIGN PATENT DOCUMENTS

| | | |
|---|---|---|
| DE | 41 18 154 A1 | 12/1992 |
| DE | 44 05 607 A1 | 8/1995 |
| DE | 199 34 654 A1 | 2/2000 |
| DE | 101 40 134 A1 | 4/2002 |

OTHER PUBLICATIONS

Horowitz and Hill, The Art of Electronics, Cambridge University Press, 1989, p. 636.*

* cited by examiner

*Primary Examiner*—Drew A Dunn
*Assistant Examiner*—Stephen J Cherry
(74) *Attorney, Agent, or Firm*—Bacon & Thomas, PLLC

(57) ABSTRACT

This invention relates to a measuring device for process technology, to be used in measurement and/or cleaning and/or calibration installations in the area of process automation, for measuring pH-values and/or redox potentials and/or other process parameters, and has a central unit, with which at least one measurement module is connectable. Every measurement module is selectable by the central unit by a selection line assigned thereto.

11 Claims, 1 Drawing Sheet

MEASURING DEVICE FOR PROCESS ENGINEERING AND OPERATING METHOD FOR A MEASURING DEVICE

FIELD OF THE INVENTION

The present invention relates to a measuring device for process technology useful in measuring- and/or cleaning- and/or calibration-installations in the field of process automation for measuring pH and/or redox potentials and/or other process parameters with a central unit, wherein at least one measurement module is connectable with the central unit.

BACKGROUND OF THE INVENTION

The present invention also relates to an operating method for a measuring device for process technology useful in measuring- and/or cleaning- and/or calibration-installations in the field of process automation for measuring pH and/or redox potentials and/or other process parameters with a central unit.

Measuring devices of the type named above often include a possibility for expansion based on measurement modules, which e.g. are equipped with different sensors and can also be integrated later into the central unit later, respectively be connected therewith.

For communicating with the measuring device, known measurement modules have complex communication means, such as e.g. special interface controllers, which are correspondingly expensive, or a computational unit of the measurement module must itself carry out the communicating with the central unit, whence correspondingly fewer resources are available for capture of measurement data.

SUMMARY OF THE INVENTION

An object of the present invention is to provide an improved measuring device, as well as an improved operating method for a measuring device, wherein measurement modules can communicate flexibly with the central unit and must have only very little built-in intelligence, in order to participate in a data communication with the central unit.

In a measuring device of the type named above, this object is achieved according to the invention in that each measurement module is selectable by the central unit on the basis of a selection line assigned thereto.

On this selection line, the particular measurement module is signaled by the central unit that it has been selected by the central unit for the communication, respectively for the data transfer. The use of the signaling of the invention via the selection line assigned to the measurement module enables omission of a complicated evaluation electronics in the measurement module. The electronics of the measurement module must merely monitor a logical state of the selection line assigned to the measurement module.

If the central unit has a module housing, into which the measurement modules can be integrated by insertion into plug-in locations provided therefor, it is possible to assign a selection line of the central unit to each plug-in location. The connecting of the selection line with the measurement module then occurs upon the insertion of the measurement module into the plug-in location of the central unit.

An advantageous form of embodiment of the present invention is characterized in that all measurement modules are connectable with the central unit over a central transmission line.

A signal transmitted from the central unit on the central transmission line arrives in this way simultaneously at all measurement modules connected to the central unit. However, only the measurement module selected by the central unit by the selection line assigned to it utilizes the signal transmitted from the central unit over the central transmission line; the other measurement modules are not selected and therefore do not utilize the signal transmitted by the central unit over the central transmission line.

Another advantageous form of embodiment of the present invention is characterized in that each measurement module has a module transmission line. A measurement module selected by the central unit via the particular selection line can transmit data over this module transmission line to the central unit. For example, each module transmission line of a measurement module connected to the central unit can be connected to a separate data input of the central unit.

Very advantageous is another form of embodiment of the present invention, wherein the module transmission lines of the measurement modules are connectable with the inputs of a multiplexer, wherein the output of the multiplexer is connectable with the central unit, and wherein the multiplexer is controllable via the selection lines.

The use according to the invention of a multiplexer makes it possible, under control of the multiplexer with the help of the selection lines, to switch onto the output of the multiplexer that module transmission line out of the module transmission lines of the measurement modules which corresponds to the measurement module selected by the central unit by means of the selection lines.

Very advantageous in this form of embodiment is the double usage of the selection lines, on the one hand, for selection of a measurement module, and, on the other hand, for controlling the multiplexer.

For special cases of application, the central unit may simultaneously select a plurality of measurement modules by means of the particular selection lines, so that this plurality of measurement modules can simultaneously receive and utilize a signal sent from the central unit on the central transmission line. In this case, in using a multiplexer for the just explained bundling of the module transmission lines, it must be assured that none of the plural, simultaneously selected measurement modules answers.

Alternatively thereto, it is possible to so configure the multiplexer that none of the inputs connected with the module transmission lines of the measurement modules is forwarded onto the output of the multiplexer and thus to the central unit, once more than one selection line is activated.

The simultaneous selection of plural measurement modules can be used e.g. for simultaneously sending initialization messages at system start of the central unit in a kind of broadcast to all measurement modules connected to the central transmission line of messages which require no acknowledgment of the measurement modules. Additionally, in this way, a report can be transmitted to all measurement modules signaling a malfunction in the central unit or the like.

As another solution of the object of the present invention, it is provided in an operating method for a measuring device of the above-named type, that the measurement module is selected by the central unit by means of a selection line assigned to the measurement module.

A further advantageous embodiment of the operating method of the invention provides that a multiplexer is controlled by the selection lines in such a manner that data sent over a module transmission line of the selected measurement module is forwarded via the multiplexer to the central unit.

According to the invention, it is provided in another form of embodiment of the operating method that data sent from the central unit is transmitted to all measurement modules over a central transmission line.

Especially advantageous is a further variant of the operating method of the invention, wherein data sent from the central unit are utilized only in the measurement module selected by means of the selection line.

A further form of embodiment of the operating method of the invention provides that the measurement modules are periodically selected by the central unit for communication or data transmission. This measure assures that data possibly arising in the measurement modules, such as e.g. measurement data of sensors or calculation results, or the like, can be regularly collected by the central unit and evaluated.

Additionally, it is possible in this way to load the measurement modules periodically with control data, which are preferably transmitted via the central transmission line from the central unit to the respective measurement modules.

The periodic selection of the measurement modules by the central unit for a certain selection time can be represented expediently by time slices, the size of which corresponds to the duration of the selection time per measurement module. These time slices are assigned to the individual measurement modules by the central unit.

Thus, the size of the time slices determines for what length of time a measurement module is selected by the central unit and can communicate with the central unit, before the central unit selects a next measurement module for communication.

Quite especially advantageous is when the measurement modules, in a further form of embodiment of the operating method of the invention, are aperiodically selected by the central unit.

The aperiodic selection of measurement modules makes it possible to reduce the time of latency present because of the principle involved. The time of latency results from the selecting of other measurement modules between the selection of a first measurement module and the renewed selection of this first measurement module.

Very advantageous for an aperiodic selection of measurement modules is the choosing of a cycle time for the communication of the central unit with the measurement modules such that the sum of all time slices periodically assigned to the measurement modules is appreciably smaller than the total cycle time.

The remaining free time within the cycle can be used to select any measurement modules aperiodically. This is especially very advantageous, when data—e.g. because of sporadically occurring events—must be transmitted to, and/or read from, a measurement module with minimum delay.

Very advantageous also is the periodic selection by the central unit of different measurement modules for different selection times. This means that different measurement modules each receive differently large time slices. This enables a prioritizing of the data transmission between the measurement modules and the central unit.

Especially advantageous in this case is also the changing of the length of the selection times, i.e. the size of the time slices assigned to the measurement modules. In this way, it is, in principle, possible to change the prioritizing of the data communications during the operation of the central unit and to dynamically adapt to changing requirements. Thus, a measurement module that is inactive for most of the time, but which, when active, must transmit very large amounts of data to the central unit, can transfer these amounts of data, if necessary, rapidly to the central unit, without burdening the communication between the central unit and the remaining measurement modules, when it is inactive.

A further advantage in this case is that the measurement module does not have to have its own, large, data memory, since it can, as already indicated, transmit determined data, if necessary, rapidly to the central unit.

Another possibility for prioritizing the communication of the measurement modules with the central unit is to have individual measurement modules be selected a plural number of times within a cycle, i.e. thus that plural time slices are assigned to these measurement modules within a cycle. Besides the aperiodically assigned time slices, plural time slices can be assigned to a measurement module, even in the case of the periodic communication, and these time slices can also have differing sizes.

A further solution of the object of the present invention is provided by a measurement device, having at least one measurement module.

It is also possible, instead of a measurement module, to connect another device, such as, for example, a computing unit or some other equipment expanding the functionality of the central unit. The computing unit communicates with the central unit in the above described manner and need not necessarily serve for registering measurement data or be limited in its functionality to the registering of measurement data.

Likewise, it is possible that a measurement data preprocessing and/or a measurement data processing occur(s) in a measurement module, respectively in a computing unit.

Further features, possibilities of application and advantages of the invention will become apparent on the basis of the following description of examples of embodiments of the invention, as illustrated in the figures of the drawing. Therein, all described or illustrated features, whether alone or in any combination, form the subject matter of the invention, independently of their summarization in the patent claims or the examples in which they were presented, as well as independently of their formulation, respectively illustration, in the description, respectively in the drawing.

DESCRIPTION OF THE PREFERRED EMBODIMENT

Figure 1:
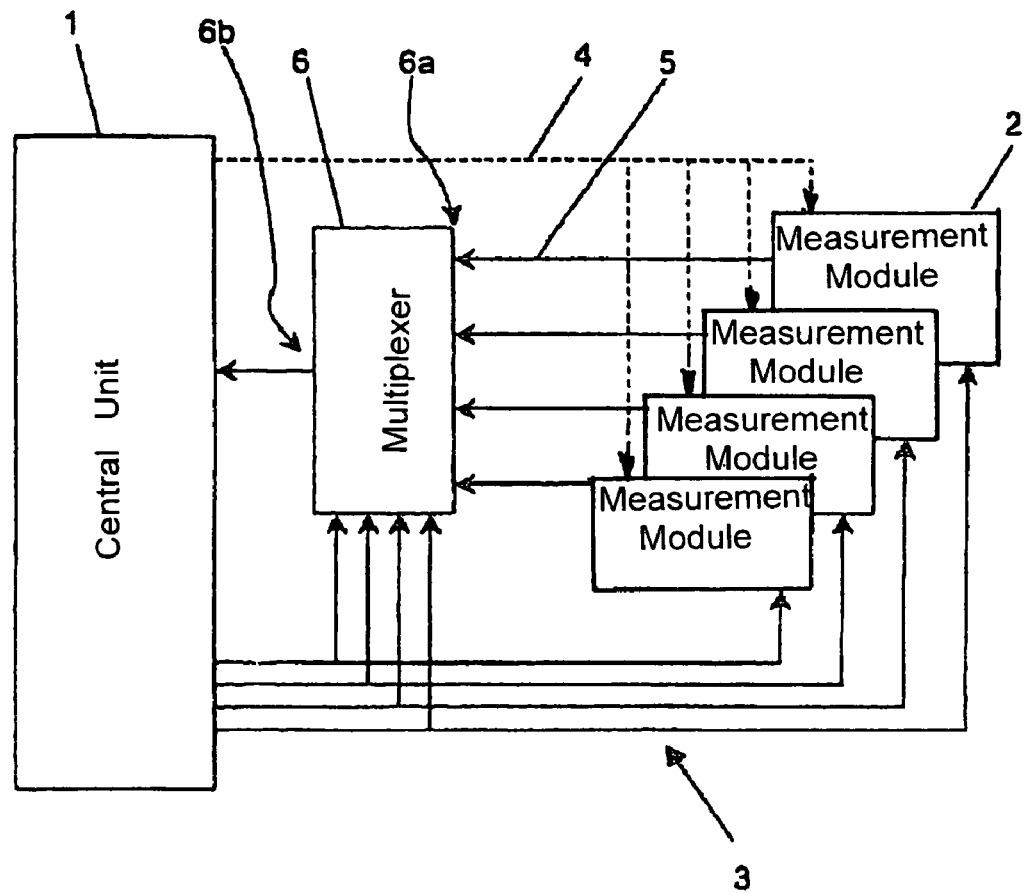
FIG. 1 shows a measuring device of the invention.

The measuring device of FIG. 1 includes a central unit 1, to which a plurality of measurement modules 2 are assigned.

All measurement modules 2 are connected with the central unit 1 over a central transmission line 4 indicated in FIG. 1 by a dashed line. The central transmission line 4 serves for transmitting a signal, respectively data, from the central unit 1 to the measurement modules 2. All measurement modules simultaneously receive the data transmitted from the central unit 1 over the central transmission line 4.

Furthermore, each measurement module 2 is assigned its own selection line 3, which connects the measurement module 2 with the central unit 1. The selection lines 3 serve to enable selection of their measurement modules by the central unit 1 for communication or data transfer.

Only one measurement module 2 selected in this way utilizes the signal transmitted by the central unit 1 over the central transmission line 4. The non-selected measurement modules 2 do not utilize the signal from the central unit 1.

For the data transfer from the measurement modules 2 to the central unit 1, each measurement module 2 is assigned a module transmission line 5. As can be seen in FIG. 1, the module transmission lines 5 of the measurement modules 2 are connected with the inputs 6a of a multiplexer 6. The output 6b of the multiplexer 6 is connected with the central unit 1.

The multiplexer 6 serves for selecting one of the module transmission line 5 of the measurement modules 2 and for connecting such via output 6b of the multiplexer 6 with the central unit 1. The control of the multiplexer 6 for selecting the module transmission line 5 occurs via the selection lines 3, which act also on the multiplexer 6, as can be seen in FIG. 1. Thus, by the selection lines, on the one hand, a measurement module is selected by the central unit 1 for communication, and, one the other hand, the multiplexer 6 is controlled via the selection lines 3.

In this way, it is possible always to connect that module transmission line 5 from the inputs 6a of the multiplexer 6 through the output 6b of the multiplexer 6 to the central unit 1 that corresponds to the measurement module 2 selected by means of the selection lines 3.

Thus, a communication between the selected measurement module 2 and the central unit 1 is enabled.

In principle, it is also possible to select all or at least a plurality of measurement modules 2 simultaneously via the selection lines 3. Even in this operational state, however, only one of the selected measurement modules 2 can communicate over its module transmission line 5 and the multiplexer 6 with the central unit 1.

Alternatively to this, it is possible to configure the multiplexer 6 such that none of the inputs 6a connected with the module transmission lines 5 of the measurement module 2 is forwarded to the output 6b of the multiplexer 6 and thus to the central unit 1, as soon as more than one selection line 3 is activated.

It is possible that special initialization commands or other commands indicating special operational conditions, such as e.g. errors and the like, are transmitted to all measurement modules 2 in this mode of operation of the central unit 1, whereby a kind of broadcast is realized.

Apart from the above-described, special operational conditions, only that measurement module 2 specially selected by the central unit 1 over the selection lines 3 can communicate over its module transmission line 5 with the central unit 1.

In order, nevertheless, to be able to address plural measurement modules, a time control is provided in the central unit 1 for the communication with the measurement modules 2.

The time control provides, quite generally, that all measurement modules 2 connected with the central unit 1 are selected sequentially by the central unit 1 via the separate selection lines 3 assigned to them. In this, the selection of a particular measurement module 2 is maintained by the central unit 1 for a certain selection time Ta. During this time, it is possible for the selected measurement module 2 to exchange data with the central unit 1. The data exchange can be executed at different data rates, depending on which measurement module 2 has been selected.

For recognizing a measurement module 2 newly arranged in the measuring device, it is also possible to query the new measurement module 2 successively with different data rates, according to an identification pattern. As soon as the central unit 1 receives a valid identification pattern back from the new measurement module 2, the information connected therewith about the new measurement module 2 is stored and used for further communications with it. Subsequently, the selection time Ta is given to the new measurement module 2. This enables an integration of measurement modules into a measuring device of the invention, without it being necessary that the measurement module 2 be specially adjusted to the communication parameters, such as e.g. the selection time Ta, installed in the measuring device.

Following passage of the selection time Ta, a next measurement module is selected by the central unit 1 over the selection lines 3. This selection is likewise maintained for the selection time Ta.

As soon as all measurement modules 2 connected to the central unit 1 have been selected once in this way, a new communication cycle begins, and the first measurement module 2 is selected anew by the central unit 1 for communication.

Different selection times Ta, Tb, Tc can also be assigned to the individual measurement modules, in order to effect a prioritizing of the communications.

Figure 2:
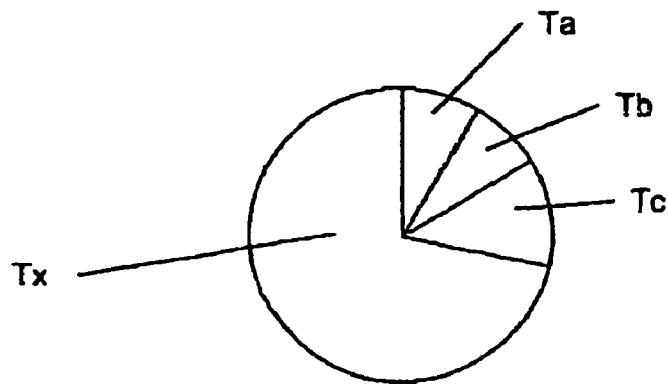
FIG. 2 shows schematically the division of a communication cycle into different selection times.

The selection times Ta, Tb, Tc assigned to the individual measurement modules 2 can also be thought of as time slices, the sizes of which are proportional to the duration of the respective selection times Ta, Tb, Tc, and which are represented graphically in FIG. 2 in the context of a pie chart.

The selection times Ta, Tb and Tc are assigned to three different measurement modules 2 (FIG. 1) and indicate that these three measurement modules 2 are periodically selected by the central unit 1, namely once in every communication cycle. This selection sequence results from travelling the pie chart of FIG. 2 in a mathematically negative sense, with the communication cycle starting with the selection time Ta.

The selection time Tx, likewise indicated in FIG. 2 and being the time difference between the sum of the selection times Ta, Tb, Tc and the cycle time Ta+Tb+Tc+Tx of the communication cycle, corresponds to a free time slice and is used by the central unit 1, for instance, to select individual measurement modules 2 aperiodically.

This is especially useful, when additional data needs to be transferred from the central unit 1 to a particular measurement module 2 and the slice of time allotted to the measurement module 2 within the bounds of the periodic communication is not large enough for transferring the particular data sufficiently rapidly, e.g. within one communication cycle.

As already shown, a prioritizing of the communication between the central unit 1 and the measurement modules 2 is possible by changing the sizes of the time slices. In the present case, for example, the selection time Tc is greater than the selection time Tb.

Beyond this, it is also possible to assign to a measurement module 2 plural time slices of equal or different sizes within one communication cycle.

For example, a measurement module 2, which contains a spectrometer and which must transmit to the central unit 1 relatively large amounts of data per communication cycle compared to a temperature sensor, can receive four time slices of selection time Ta within one communication cycle, while a measurement module with a temperature sensor, which evaluates a temperature changing only very slowly, receives only one time slice of selection time Ta.

Especially advantageous also is the changing of the selection times Ta, Tb, Tc. In this way, it is, in principle, possible to change the prioritization of the communication during the operation of the central unit 1 and to adapt dynamically to changing demands. In this way, a measurement module 2, which is inactive for most of the time, but which must, when it becomes active, transmit very large amounts of data to the central unit 1, can, in the case of need, transmit these amounts of data quickly to the central unit 1, without burdening the communication between the central unit 1 and the remaining modules 2, during the time that it is inactive.

A further advantage in this case is that the measurement module 2 does not need a large data memory of its own, since it can transfer obtained data—as already shown—in the case of need, quickly to the central unit 1 and does not need to buffer data itself over any extended period of time.

A further possible embodiment of the invention concerns a measuring system having a measuring device equipped with at least one measurement module 2.

In another form of embodiment of the invention, it is possible, instead of the central transmission line 4 and the module transmission line 5 for each measurement module 2, to provide a bidirectional communications connection (not shown) between each measurement module 2 and the multiplexer 6. In this case, also the output 6b of the multiplexer 6 is connected by a bidirectional communications connection with the central unit 1. The multiplexer 6 is, in this case, controlled by the selection lines 3, whereby one of the measurement modules 2 is selected. In this case, an explicit selection of the measurement module 2, as in the case of the examples discussed to this point, is not required, so that the selection lines 3 only still connect the central unit 1 with the multiplexer 6 and do not need to act on every measurement module 2.

Very advantageous is the case of another form of embodiment of the invention, where, before a data transmission between the central unit 1 and a measurement module 2, control commands are sent to the multiplexer 6, where they are evaluated and effect the selection of a measurement module 2. In this form of embodiment, the selection lines 3 can be completely eliminated.

The invention claimed is:

1. A measuring device for process technology, to be used in measurement and/or cleaning and/or calibration installations in the area of process automation, for measuring pH-values and/or redox potentials and/or other process parameters, comprising:
   a central unit;
   a central transmission line;
   at least one measurement module connected to said central unit by said central transmission line for transferring a data signal over said central transmission line from said central unit to said measurement module;
   a multiplexer; and
   a selection line associated with each measurement module for connecting its associated measurement module to said central unit and to said multiplexer, wherein:
   each measurement module is selectable by said central unit by one of said selection lines;
   said central transmission line and the selection line being different lines;
   each measurement module having a module transmission line connecting the measurement modules with inputs of said multiplexer;
   the multiplexer having an output, which is connectable with said central unit; and
   said multiplexer is controllable via said selection lines.

2. An operating method for a measuring device for process technology, to be used in measurement and/or cleaning and/or calibration installations in the area of process automation, for measuring pH-values and/or redox potentials and/or other process parameters, having a central unit, a multiplexer and a plurality of measurement modules connected with the central unit; comprising the steps of:
   providing a selection line for each measurement module connecting the plurality of measurement modules to the central unit;
   selecting a measurement module by the central unit and an associated selection line;
   utilizing data sent from the central unit over a central transmission line only in the measurement module selected by means of the associated selection line; and
   controlling the multiplexer by the selection lines such that data transmitted over a module transmission line of the selected module are forwarded via the multiplexer to the central unit.

3. The operating method according to claim 2, wherein:
   different measuring modules are selected for different selection times periodically by the central unit.

4. The operating method according to claim 3, wherein:
   the selection times are changed.

5. A measuring device for process technology, to be used in measurement and/or cleaning and/or calibration installations in the area of process automation, for measuring pH-values and/or redox potentials and/or other process parameters, comprising:
   a plurality of measurement modules;
   a central unit;
   a multiplexer;
   a plurality of selection lines; and
   a central transmission line, wherein:
   all said measurement modules are connected to said central unit by said central transmission line for transferring a data signal over said central transmission line from said central unit to all measurement modules;
   each measurement module is assigned its own selection line connecting the measurement module to said central unit,
   each measurement module is selectable by said central unit by said selection line, wherein only the measurement module selected by the central unit by the selection line assigned to it utilizes the data signal transmitted from the central unit over the central transmission line;
   said central transmission line and the selection line being different lines;
   each measurement module having a module transmission line connecting the measurement modules with inputs of said multiplexer, the multiplexer having an output, which is connectable with the central unit; and
   said multiplexer is controllable via said selection lines.

6. The measuring device according to claim 5, wherein:
   the selection lines assigned to each measurement module acts also on said multiplexer for controlling said multiplexer.

7. The measuring device according to claim 5, wherein:
   several measurement modules are selectable simultaneously by means of the selection lines assigned to each of said measurement modules, so that said several measurement modules can simultaneously receive and utilize a data signal sent from the central unit on said central transmission line.

8. The measuring device according to claim 7, wherein:
   said multiplexer is configured such that none of the inputs connected with said module transmission lines of the measurement modules is forwarded to the output of said multiplexer and thus to said central unit as soon as more than one selection line is activated.

9. The measuring device according to claim 5, wherein:
   all measurement modules receive the data transmitted from said central unit over said central transmission line simultaneously.

10. An operating method for a measuring device for process technology, to be used in measurement and/or cleaning and/or calibration installations in the area of process automation, for measuring pH-values and/or redox potentials and/or other process parameters, having a central unit, and a plurality of measurement modules connected with the central unit, comprising the steps of:
- providing a selection line for each measurement module connecting the plurality of measurement modules to the central unit;
- transmitting data from the central unit over a central transmission line to all measurement modules;
- selecting a measurement module by the central unit and an associated selection line;
- utilizing data sent from the central unit over the central transmission line only in the measurement module selected by means of the associated line; and
- controlling a multiplexer by the selection lines such that data transmitted over a module transmission line of the selected measurement module are forwarded via the multiplexer to the central unit, wherein;
- different measuring modules are selected for different selection lines periodically by the central unit; and the selection times are changed.

11. The operating method as claimed in claim 10, wherein:
the measurement modules are periodically selected by the central unit.

* * * * *